(12) United States Patent
Nelson

(10) Patent No.: US 11,370,878 B2
(45) Date of Patent: *Jun. 28, 2022

(54) SYSTEMS AND METHODS FOR PRODUCTION OF ARTIFICIAL EUMELANIN

(71) Applicant: THE BOARD OF REGENTS FOR OKLAHOMA STATE UNIVERSITY, Stillwater, OK (US)

(72) Inventor: Toby Larue Nelson, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/019,920

(22) Filed: Sep. 14, 2020

(65) Prior Publication Data

US 2020/0407490 A1 Dec. 31, 2020

Related U.S. Application Data

(62) Division of application No. 16/530,136, filed on Aug. 2, 2019, now Pat. No. 10,774,175, which is a division of application No. 15/127,155, filed as application No. PCT/US2015/021216 on Mar. 18, 2015, now abandoned.

(60) Provisional application No. 61/954,756, filed on Mar. 18, 2014.

(51) Int. Cl.
| | | |
|---|---|---|
| *C07D 209/04* | (2006.01) | |
| *C08G 61/12* | (2006.01) | |
| *C07D 209/24* | (2006.01) | |
| *C08G 73/06* | (2006.01) | |
| *C09D 179/04* | (2006.01) | |
| *C07D 209/42* | (2006.01) | |
| *C09D 5/24* | (2006.01) | |
| *C09D 165/00* | (2006.01) | |
| *H01L 51/00* | (2006.01) | |
| *C08K 3/04* | (2006.01) | |
| *H01L 51/05* | (2006.01) | |
| *H01L 51/42* | (2006.01) | |
| *H01L 51/50* | (2006.01) | |

(52) U.S. Cl.
CPC ......... *C08G 61/124* (2013.01); *C07D 209/24* (2013.01); *C07D 209/42* (2013.01); *C08G 73/0672* (2013.01); *C09D 5/24* (2013.01); *C09D 165/00* (2013.01); *C09D 179/04* (2013.01); *H01L 51/0035* (2013.01); *H01L 51/0043* (2013.01); *C08G 2261/12* (2013.01); *C08G 2261/135* (2013.01); *C08G 2261/1424* (2013.01); *C08G 2261/1426* (2013.01); *C08G 2261/312* (2013.01); *C08G 2261/3241* (2013.01); *C08G 2261/3328* (2013.01); *C08G 2261/76* (2013.01); *C08G 2261/91* (2013.01); *C08G 2261/92* (2013.01); *C08G 2261/95* (2013.01); *C08K 3/041* (2017.05); *C08K 3/042* (2017.05); *C08K 3/045* (2017.05); *H01L 51/0007* (2013.01); *H01L 51/0558* (2013.01); *H01L 51/42* (2013.01); *H01L 51/50* (2013.01)

(58) Field of Classification Search
CPC .................................................. C07D 209/24
See application file for complete search history.

(56) References Cited

U.S. PATENT DOCUMENTS

| | | | |
|---|---|---|---|
| 7,091,220 B2 * | 8/2006 | Gerlach | A61P 25/00 514/323 |
| 10,774,175 B2 * | 9/2020 | Nelson | H01L 51/0043 |

* cited by examiner

*Primary Examiner* — Golam M Shameem
(74) *Attorney, Agent, or Firm* — Fellers, Snider, Blankenship, Bailey & Tippens, P.C.; Terry L. Watt

(57) ABSTRACT

"Black" photoactive materials that comprise synthetic eumelanin polymers are provided, as are methods of making and using the polymers. The synthetic eumelanin polymers are made from the plant oil vanillin, and exhibit defined structural and chemical characteristics (e.g. homogeneity, solubility, etc.) that make them suitable for use in devices that require photoactive materials, such as solar cells.

3 Claims, 10 Drawing Sheets

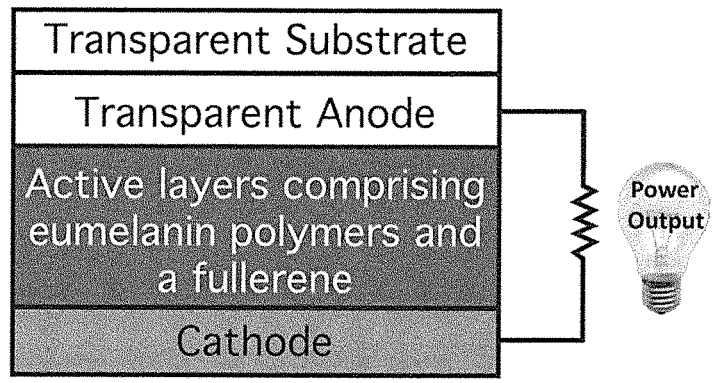
*Figure 14A*
*Figure 14B*
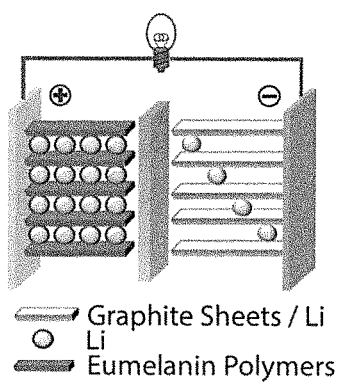
*Figure 14C*
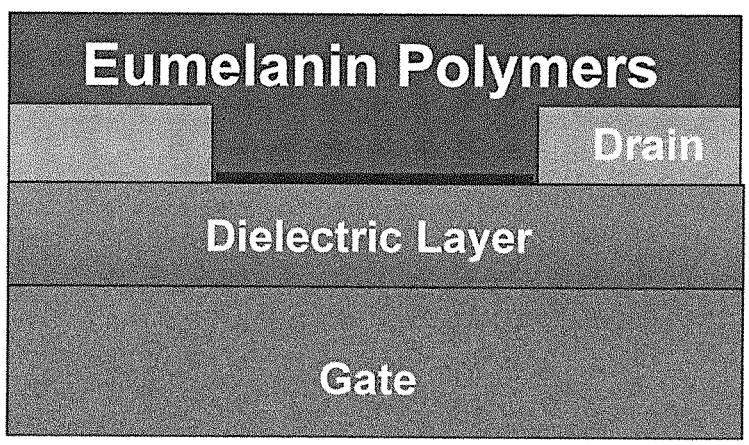
*Figure 14D*

SYSTEMS AND METHODS FOR PRODUCTION OF ARTIFICIAL EUMELANIN

CROSS REFERENCE TO RELATED APPLICATIONS

This application is a divisional of U.S. patent application Ser. No. 16/530,136, filed Aug. 2, 2019, which application is a divisional of abandoned U.S. patent application Ser. No. 15/127,155, filed Sep. 19, 2016, which application was a 371 entry into the U.S. from PCT/US2015/021216, filed Mar. 18, 2015, which application claimed the benefit of U.S. Provisional Patent Application Ser. No. 61/954,756 filed on Mar. 18, 2014, and incorporates said applications by reference into this document as if fully set out at this point.

BACKGROUND OF THE INVENTION

Field of the Invention

This invention generally relates to "black" photoactive materials that comprise synthetic eumelanin polymers. In particular, the invention relates to methods of making synthetic eumelanin polymers from vanillin, and their use in devices that require photoactive materials, such as solar cells.

Background

Our world faces an imminent global energy crisis that will be the defining challenge for this generation of scientists and engineers. The search for alternative fuels to power the future and alleviate human effects on the environment is a daunting task. Solar energy is foremost of these renewable energy sources due to its potential for providing nearly 274,000 terawatts of power per year (which exceeds the world energy consumption by a factor of about 17,000 times. Much progress has been made in the development of inorganic based solar cells such as those made from silicon. Since the invention of conductive polymers, scientists have been trying to provide replacements for inorganic photovoltaic materials that are comprised of inexpensive plastics. Conductive plastics have the potential to create economical, processable and flexible alternatives to harvest energy from sunlight. The most prominently studied active layer in polymer solar cells is a regioregular poly(3-hexylthiophene) (rr-P3HT) and [6,6]-phenyl-C61-butyric acid methylester (PCBM, derivative of C60) bulk heterojunction. Unfortunately, insufficient light absorption by rr-P3HT due to its mismatch with the solar spectrum limits solar performance. To improve solar power conversion efficiencies of polymer solar cells, there is a critical need to design and synthesize novel conducting polymers that absorb broadly and at the longer wavelengths that are required to better enable robust usage of the solar spectrum.

Melanins are a class of naturally occurring pigmentary macromolecules found in mammals. Compounds have a high degree of conjugation rendering them a powerful radiation absorber with broadband photon absorption spectrum that extends from the ultraviolet into the infrared range. Eumelanin, the black-brown variety of melanin that is responsible for dark-colored eyes, hair, and skin, acts as a natural photoprotector from the harmful radiation from the sun. Eumelanins are thought to be complex heterogeneous networks of randomly cross-linked biopolymers composed of two building blocks, 5,6-dihydroxyindole and 5,6-dihydroxyindole-2-carboxylic acid, produced by oxidative polymerization of the two monomers. Eumelanin is very resistant to damage caused by high temperature, chemical stresses, reactive oxygen species, ultraviolet radiation, X-rays, gamma rays, and alpha and beta particles. It has extremely high absorption from 200 to 600 nm (extinction coefficient=2000-7600 $cm^{-1}M^{-1}$) and trails with a moderate absorption up to 820 nm (500-800 $cm^{-1}M^{-1}$).

Interestingly, eumelanins are organic semiconductors. While the use of eumelanins as organic semiconductors is an attractive proposition, unfortunately, natural eumelanin and eumelanin synthesized by existing prior art methods are extremely heterogeneous, insoluble in most solvents and do not have a well-defined structure. Thus elucidation of structure-property relationships is challenging or impossible. In the absence of other forms of eumelanin, current research involving electronic devices based on eumelanin has only employed insoluble eumelanin pellets or thin, brittle films displaying very poor morphologies. Thus, it has not been possible to take advantage of the semiconducting properties of eumelanins.

Heretofore, as is well known in the eumelanin synthesis arts, there has been a need for an invention to address and solve the disadvantages of prior art approaches. Accordingly it should now be recognized, as was recognized by the present inventors, that there exists, and has existed for some time, a very real need for synthetic eumelanins and methods of making and using synthetic eumelanins that would address and solve the above-described and other problems.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

The present disclosure provides synthetic eumelanins that are homogeneous in compositions, soluble in a wide variety of solvents and which have a well-defined structure. Methods of making the synthetic eumelanins, a new core molecule that is used in the synthesis methods, and methods of using the synthetic eumelanins are also provided. In one aspect, the starting material for the synthesis of the synthetic eumelanins is advantageously a plant oil, vanillin, extracted from vanilla beans. Briefly, vanillin first passes through a series of reactions to form the novel core compound 4,7-dibromoindole (methyl 4,7-dibromo-5,6-dimethoxy-N-methyl-1H-indole-2-carboxylate), and the 4,7-dibromoindole core molecule serves as a building block for production of well-defined, high performance conjugated polymers. In contrast to thin film fabrication methods that depend on petroleum-based polymers, the present methods and compounds do not involve the use of petroleum starting materials/feedstocks and thus represent a sustainable technology. The synthetic eumelanin polymers are used, for example, as "black" photoactive materials for a variety of applications e.g. to produce thin films used in solar cells, transistors, etc.

According to an embodiment, there is provided an indole as depicted in Formula I:

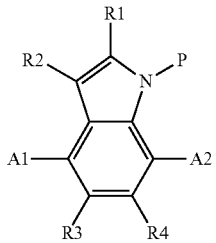

Formula I

Where, R1, R2, R3 and R4 vary independently and may be the same or different, and can be H, substituted or unsubstituted alkyl, substituted or unsubstituted alkylester, substituted or unsubstituted alkoxy, substituted or unsubstituted aryloxy moiety, substituted or unsubstituted polyethylene glycol (PEG), a macroinitator, a polymer or a crosslinker; A1 and A2 may be the same or different and are halogen, $R_3Sn$, $B(OR)_2$, OTf, $SiR_3$, or $Si(OR)_3$; and P is H or a protecting moiety.

According to another embodiment, there is taught herein a method of making methyl 4,7-dibromo-5,6-dimethoxy-N-methyl-H-indole-2-carboxylate (DBI), comprising reacting vanillin

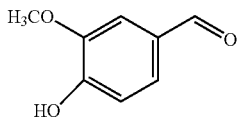

to form DBI

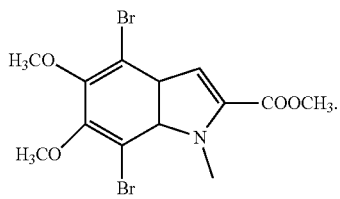 [SMILES: COC(=O)C1=CC2C(Br)=C(OC)C(OC)=C(Br)C2N1C]

According to still another embodiment, there is provided a polymer of Formula III

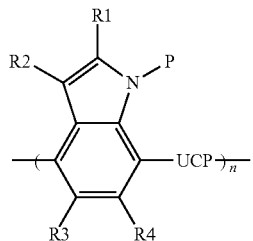

Formula III where R1, R2, R3 and R4 vary independently and may be the same or different, and can be H; substituted or unsubstituted alkyl; substituted or unsubstituted alkylester; substituted or unsubstituted alkoxy: substituted or unsubstituted aryloxy; substituted or unsubstituted polyethylene glycol (PEG); a macroinitator; a polymer or a crosslinker; P is H or a protecting moiety; UCP is present or absent and if present is an unsaturated carbon pair which is connected directly to a repeat unit of the polymer or is connected indirectly to a repeat unit of the polymer through a substituted or unsubstituted aromatic; and n ranges from about 10 to about 1000.

According to a further embodiment, there is taught herein a method of forming a polymer comprising the step of reacting 4,7-dibromo-5,6-dimethoxy-N-methyl-1H-indole-2-carboxylate (DBI)

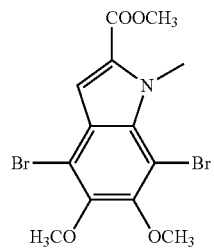

with a compound of formula X1-UCP-X2, wherein UCP is an unsaturated carbon pair and X1 and X2 are the same or different and are chemical groups capable of displacing Br and forming a covalent bond at positions 4 and 7 of said DBI.

Taught herein is an embodiment of a method of forming a polymer comprising the step of reacting 4,7-dibromo-5,6-dimethoxy-N-methyl-1H-indole-2-carboxylate (DBI)

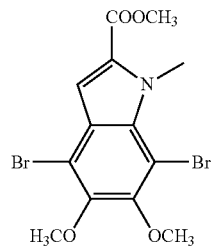

with a compound of formula

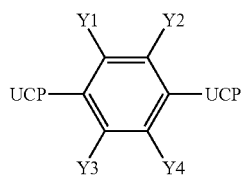

wherein UCP is an unsaturated carbon pair and wherein Y1, Y2, Y3 and Y4 are the same or different and are selected from i) H or a saturated or unsaturated, branched or unbranched, substituted or unsubstituted alkyl with from about 1 to about 30 carbon atoms; or ii) OR where R is H or a saturated or unsaturated, branched or unbranched, substituted or unsubstituted alkyl with from about 1 to about 30 carbon atoms.

Additionally taught herein is a solution comprising a plurality of unpolymerized or partially polymerized repeat units thereof; and a solvent.

Further taught herein is a method of making a photoactive semi-conducive material comprising i) applying to a substrate, a solution comprising a plurality of unpolymerized and/or partially polymerized repeat units thereof; and a solvent; and ii) allowing said solvent to evaporate from said substrate, thereby forming a photoactive semi-conducive material on said substrate.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

Other objects and advantages of the invention will become apparent upon reading the following detailed description and upon reference to the drawings in which:

FIG. 14A-D shows schematic representations of devices in which the synthetic eumelanin polymers are used. A, polymer solar cell containing an active layer comprised of eumelanin-based donor polymers and a PCBM acceptor; B, an organic light-emitting diode containing an emissive layer comprised of eumelanin polymers; C, an ion battery containing eumelanin polymers as electronic and ionic conductors; and D, a field-effect transistor containing eumelanin polymers as the charge transport materials.

DETAILED DESCRIPTION

Figure 1:
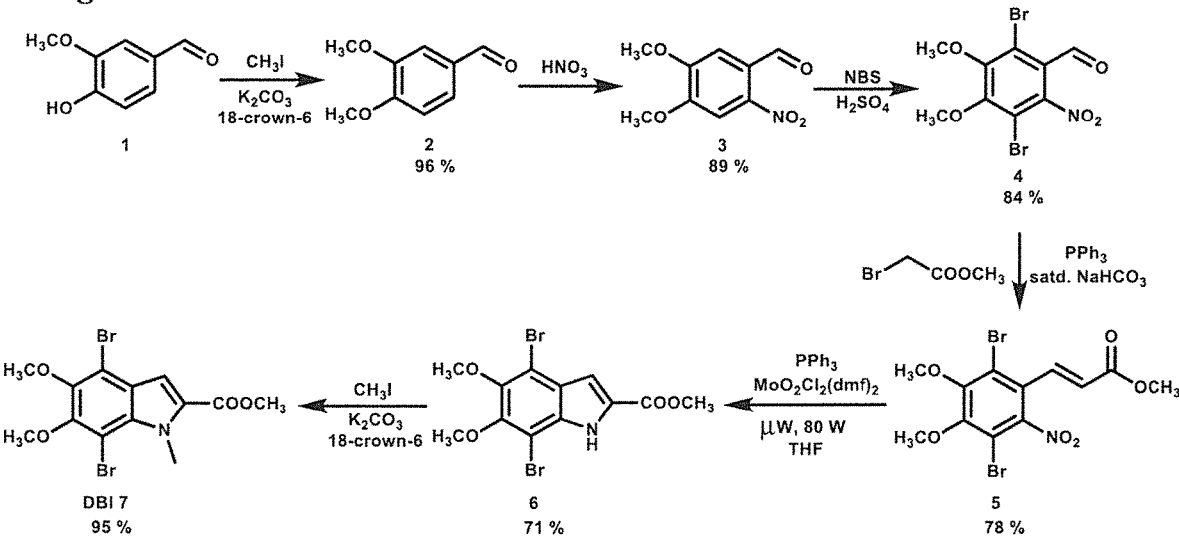
FIG. 1. Synthesis of eumelanin-inspired core (DBI) 7 from vanillin (Scheme 1).

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments so described.

The present disclosure provides novel well-defined eumelanin based polymers and synthesis routes for making the polymers. The polymers are made using a novel indole molecule which serves as a core for the polymer building blocks (subunits, repeat units, monomers), a generic representation of which is presented in Formula I below:

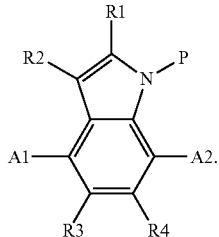

Formula I

In Formula I, R1, R2, R3 and R4 are variable groups which may be the same or different, or two or three of which can be the same while the third and/or fourth differs, and can be H, alkyl (e.g. C1 to C20 branched or unbranched, substituted or unsubstituted alkyl, etc.), an alkylester, an alkoxy moiety, an aryloxy moiety, polyethylene glycol (PEG), a macroinitator [e.g. poly(oxyethylene), poly(3-hexylthiophene), a α-methylstyrene-containing precopolymer, poly(alkoxyamine), poly(dimethylsiloxane), etc.], various a polymers or a crosslinker (e.g. bis(triethoxysilylpropyl)tetrasulfide, isocyanate-based crosslinking agents, various acrylate and phenolic crosslinkers, etc.) A1 and A2 may be the same or different and are halogens such as Br, I, F, Cl, etc. or other leaving groups such as OTf (triflate), $SiOR_3$, $SnR_3$, $B(OR)_2$, etc. P is H or a protecting moiety, e.g. an atom or group of atoms that is non-reactive or less reactive e.g. than the halogens at A1 and A2, and may be, for example, alkyl (e.g. C1 to C20 branched or unbranched, substituted or unsubstituted alkyl, etc.), PEG, carbamates, acetamides, benzyl, or tosylamide.

In one aspect, the indole core molecule is a 4,7-dibromoindole, methyl 4,7-dibromo-5,6-dimethoxy-N-methyl-1H-indole-2-carboxylate (DBI, Formula II)

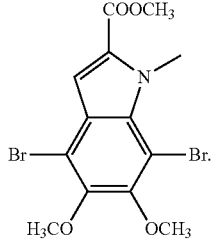

Formula II

As noted above, exemplary variations on DBI can include alternative alkoxy moieties, aryloxy moieties at either or both the methoxys; alternative halogens or other leaving groups at either or both the bromine moieties; hydrogen or other alkyls at the nitrogen moiety; substitutions with an alkyl (e.g. PEG, etc.) at the unsubstituted carbon on the five-membered ring; and alkyl or alkylesters at the site of the methyl ester moiety.

The indole core molecules of the invention are advantageously made using the natural compound vanillin as the starting material.

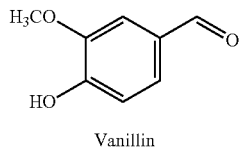 [SMILES: COc1cc(C=O)ccc1O]

Vanillin

As is evident from Formula I, the indole core molecule can be para substituted at the 4 and 7 positions by displacement of the leaving groups A1 and A2. This property, plus varying of the R1, R2, R3 and R4 groups and protecting group P, provides an avenue to making many diverse polymer subunits, as well as various copolymers and crosslinked polymer networks of defined composition, thereby providing the opportunity to tune polymer compositions to confer desired properties on the polymers. As a result, while the self-assembled synthetic eumelanin based polymers described herein do mimic the heterogeneous network formed by natural eumelanin, they also differ from and are superior to natural or prior art eumelanin in several significant ways. For example, the chemical structures of the new artificial polymers are well-defined. As described above, the polymers exhibit high tolerance to the introduction of diverse functional groups, making it possible to alter the optical and electronic properties of the polymers for different applications. For example, the polymers in general are soluble in many common solvents, including water, but can also be designed to be more or less soluble, or even insoluble, when necessary. Similar to natural eumelanin, these new polymers absorb sunlight over a broad region (e.g. from about 400 to about 800 nm), i.e. broader than that of a commonly used petroleum based photoactive polymer, rr-P3HT. However, this range can also be altered for particular applications. Other optical, electronic, chemical and physical properties of the polymers can also be adjusted by decorating the polymers at one or more variable sites, e.g. by varying the R groups of the DBI core material. The result is robust, processable synthetic eumelanin polymers with desired ranges of light absorption, charge mobility, film forming properties, reactivity or lack thereof, durability and longevity.

As used herein, "polymers" are molecules comprised of a plurality of repeat units (e.g. about 50 to 1000 or more repeat units). Polymers are thus typically of relatively high molecular weight, e.g. from at least about 5 to about 100 kDa or more in average molecular weight. Those of skill in the art will recognize that the exact Mw will vary, depending on the chemical composition of the components. Further, a product made with polymers as described herein may comprise a variety of polymers of different lengths. Those of skill in the art will also understand that polymers typically become insoluble at an average Mw of between about 100 kDa to about 150 kDa or higher, unless particular groups are introduced into the polymer to increase solubility. For example, alkyl chains may be introduced to promote solubility in hydrophobic solvents. The present polymers advantageously provide flexibility in composition so that soluble high Mw polymers (e.g. from about 100 to about 150 kDa or even higher) can be made in soluble forms. In addition, the products described herein may also comprise oligomers or a mixture of polymers and oligomers. The term "oligomer" as used herein refers to molecules of relatively low molecular weight or partially polymerized repeat units (e.g. less than about 50, 25% or even fewer repeat units) than a "polymer". Oligomers may comprise only a few repeat units (e.g. about 2 to about 50).

Synthetic Eumelanins and Methods of Making Synthetic Eumelanins

Exemplary synthetic methods for making the polymer starting materials and polymers described herein are presented in the Examples section below. In particular, Scheme 1 in FIG. 1, which is described in Example 1, shows a synthesis scheme for DBI in which vanillin is the starting material. According to the scheme, vanillin is in successive reactions methylated, nitrated, and brominated, a methoxy group is added to permit formation of a 5-membered ring, thereby forming an indole. Methylation of the ring nitrogen of the indole prevents further reaction at that atom, and thus in the final product, DBI the two Br atoms generate reactivity at the 4,7 position on the indole ring. Several steps of the method are or can be catalyzed by metals. An alternative method for making DBI is presented in Example 4.

Example 1 and Example 2 also describe the synthesis of a variety of novel small molecules based on the exemplary indole core molecule DBI, although other indole core molecules of interest as described herein, may also be used as the basis for forming small molecules. In the case of exemplary DBI, the small molecules are formed by replacing Br at positions 4 and 7 with a variable group of interest, thereby forming a disubstituted indole. The variable groups each comprise an unsaturated carbon pair covalently bonded to a phenyl substituted with an (optional) variable R group. The unsaturated carbon pair reacts with Br at positions 4 and 7 of DBI, displacing Br and forming a disubstituted indole. This generic reaction is illustrated in Scheme A below, where "UCP" represents an unsaturated carbon pair and R represents the (optional) variable group attached to the phenyl moiety.

Scheme A

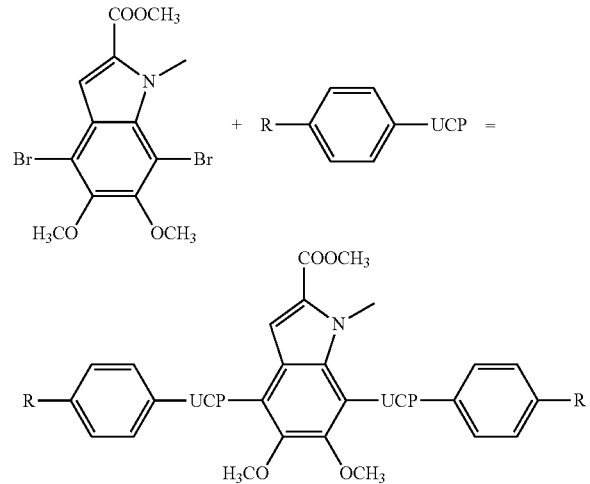

In such a reaction, the UCP may be a double or triple bond, and R=H; or a saturated or unsaturated, branched or unbranched, substituted or unsubstituted alkyl with from about 1 to about 30 total carbon atoms; an alkoxy, a halogen (e.g. F, Cl, Br, etc.); an amine ($NH_2$, N-methyl, N-ethyl, $N(CH_3)_2$, $N(CH_2CH_3)_2$, etc); hydoxyl (OH); cyano (CN); nitro ($NO_2$); $CF_3$; $SO_3H$; $CO_2H$; ester, amides, etc. In some aspects, R is H, t-butyl, O-methyl, $N(CH_3)_2$, F, CN or $NO_2$. While Scheme A shows R para to the UCP, it may also be ortho or meta. Further, the phenyl may be substituted with more than one R in some applications.

Example 1 and Example 3 also describe modifications of the exemplary indole core molecule DBI to form polymer repeat units (subunits), and polymers made therefrom, by replacing Br of DBI with a variable group of interest that is capable of attaching to and linking two DBI core molecules, thereby forming a polymeric chain of disubstituted indoles. However, those of skill in the art will recognize that other indole core molecules described herein may also be used as the starting material. In the aspect in which DBI is used, the mechanism of joining two DBI's is displacement of Br by an unsaturated carbon pair (UCP), the unsubstituted carbon pair ultimately being attached directly to two (a first and second) DBI core molecules. Scheme B generically illustrates the generation of such repeat units:

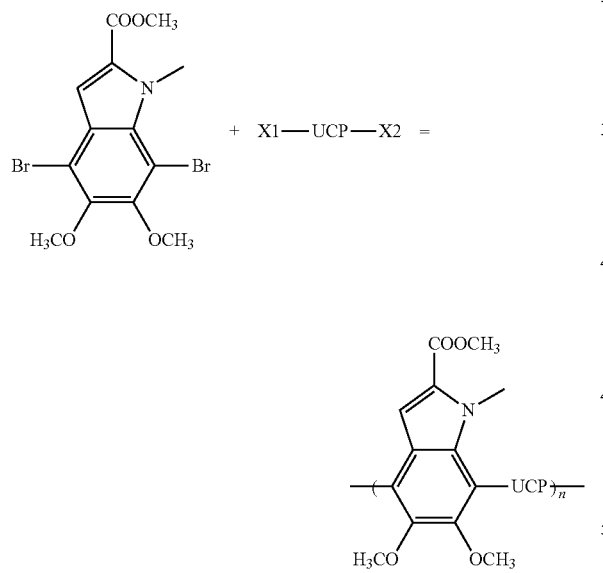

Scheme B

In some embodiments, X1 and X2 may be the same or different and are, for example and without limitation: $R_3Sn$, $B(OR)_2$, OTf, $SiR_3$, $Si(OR)_3$ etc. In Scheme B, n ranges from about 10 to about 1000, without limitation.

In a second aspect, polymer repeat units are generated by reacting DBI with a molecule that ultimately, in a polymer, is directly bonded to a first indole core via a first UCP and is indirectly bonded to a second indole core via an arylene moiety that is substituted with a second UCP. The second UCP bonds directly to the second indole core. The arylene moiety may or may not be further substituted. In some aspects, the indole core is DBI, and this aspect is represented generically Scheme C:

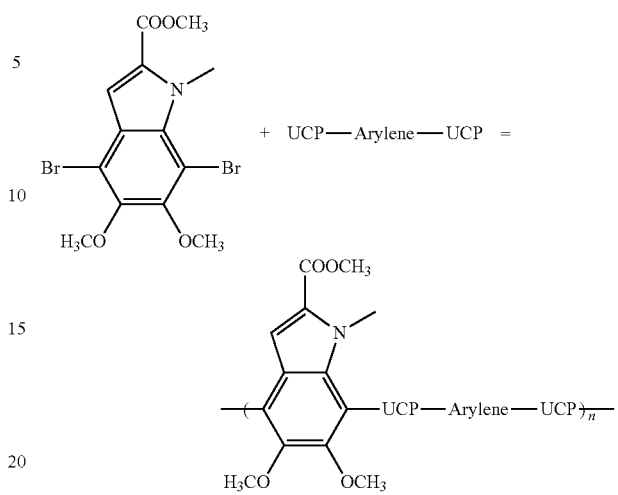

Scheme C

"Arylene" refers to a substituent of an organic compound that is derived from an aromatic hydrocarbon (arene) that has had a hydrogen atom removed from two ring carbon atoms. In Scheme C, arylene may be, for example and without limitation: unsubstituted or substituted aromatics such as benzenes, thiophenes, furan, pyrroles, pyridines, or polycyclic aromatic hydrocarbons. n ranges from about 10 to about 1000, without limitation.

In one aspect of the invention, the arylene moiety is as depicted in Scheme D:

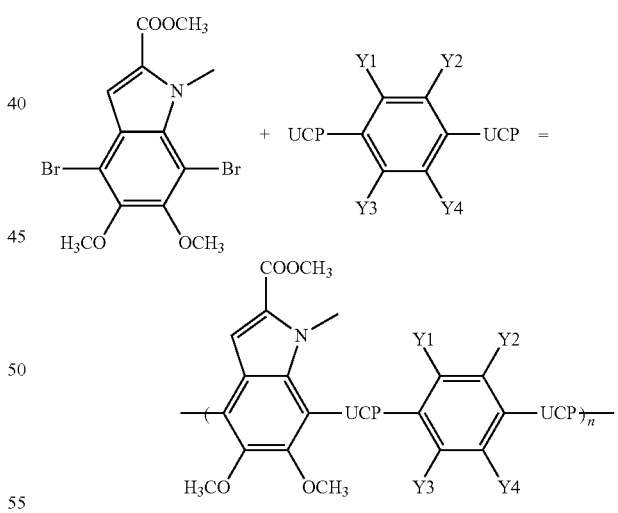

Scheme D.

In Scheme D, a copolymer is produced where the UCP is a double or triple bond and n ranges from about 10 to about 1000, without limitation. The two UDPs are generally the same, but molecules with different UCPs are also encompassed. Y1, Y2, Y3 and Y4 are variable groups whose presence is optional (i.e. one more of Y1, Y2, Y3 and Y4 may be H). If present, they may be the same or different and may be, without limitation, independently selected from: a saturated or unsaturated, branched or unbranched, substituted or unsubstituted alkyl with from about 1 to about 30 total carbon atoms; or an OR group where R is H or a saturated or unsaturated, branched or unbranched, substituted or unsubstituted alkyl with from about 1 to about 30 total carbon atoms; or CN, CF₃, or F. In some aspects, such as those depicted in FIGS. 8A and B, Y1 and Y4 are the same and are OR, where R is dodecyl or 2-ethylhexyl. n ranges from about 10 to about 1000, without limitation.

In other aspects, what is provided is a polymer that does not include unsubstituted carbon pairs as part of the linkage between repeat units. An exemplary polymer of this type is depicted in Formula IV:

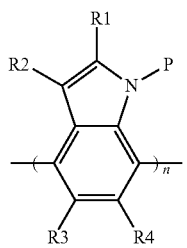

Formula IV

In Formula IV, R1, R2, R3 and R4 are variable groups which may be the same or different, or two or three of which can be the same while the third and/or fourth differs, and can be H, alkyl (e.g. C2 to C20 branched or unbranched, substituted or unsubstituted alkyl, etc.), an alkylester, an alkoxy moiety, an aryloxy moiety, polyethylene glycol (PEG) a macroinitator [e.g. poly(oxyethylene), poly(3-hexyl thiophene), a α-methylstyrene-containing precopolymer, poly (alkoxyamine), poly(dimethylsiloxane), etc.], various a polymers or a crosslinker (e.g. bis(triethoxysilylpropyl)tetrasulfide, isocyanate-based crosslinking agents, various acrylate and phenolic crosslinkers, etc.) In some aspects, R3 and R4 are RO, where R is H or a saturated or unsaturated, branched or unbranched, substituted or unsubstituted alkyl with from about 1 to about 30 total carbon atoms; PEG, a macroinitator, a polymer or a crosslinker (as above). P is H or a protecting moiety, for example, alkyl (e.g. C2 to C20 branched or unbranched, substituted or unsubstituted alkyl, etc.), PEG, carbamates, acetamides, benzyl, or tosylamide. n ranges from about 10 to about 1000, without limitation.

Uses of Small Molecules Derived from DBI

Various small molecules with advantageous light absorbing and emitting properties are described herein. Such small molecules are or can be used, for example and without limitation: as colorimetric sensors for various purposes, e.g. to measure pH, to detect the presence of various substances such as metals in water (e.g. if the R groups are OH or another suitable coordinating group); as additives (e.g. in polymer blends) for ultraviolet (e.g. sun) damage protection, either for personal use such as in sunscreens; or in paints or other products that are applied to or coated onto structures (building, cars, etc.) or substances that are exposed to UV and/or sun; or as a component of materials that are exposed to the UV and/or the sun (e.g. outdoor recreational equipment, hoses, laboratory equipment, etc); or in windows; in "plastic" protective sheeting; etc., in fibers used in UV protective clothing; etc. These molecules can also serve as probes for detection or imaging of biological analytes such as but not limited to viruses, DNA, and RNA, and recombinant forms thereof, etc.

Uses of the Synthetic Eumelanin Polymers

The synthetic eumelanin polymers disclosed herein are used in a wide variety of applications and devices. Generally, the application and devices are any in which a photoactive material is required or desired, including but not limited to: solar cells; transistors and field effect transistors (e.g. for radio-frequency identification (RFID) tags, for security, anti-counterfeiting and logic devices, etc.); fuel cells; lighting (e.g. in plastic while lighting, displays e.g. screens for television, computers, cell phones, watches, etc.; light emitting diodes such as polymeric light emitting diodes (PLEDs) and organic light emitting diodes (OLEDs); various sensors and biosensors; circuitry; thermoelectrics and organic electronics; pigment particles for a variety of coating materials e.g. conductive coatings; metal remediation of drinking water (metal coordinating groups such as OH may be introduced); actuators; electrostatic shields; electromagnetic shields;

Solar Cells

According to one aspect of the invention, well-defined organic soluble eumelanin-based polymers are introduced as novel "black" photoactive donor materials for incorporation in bulk heterojunction polymer solar cells, for example, monolithically linked or mechanically stacked tandem solar cells. The proposed materials offer the advantage of harvesting more solar radiation than prior art polymers and they can be decorated with functionalities for tuning the electronic and physical properties such as charge mobility and film-forming properties. Enhanced solar power conversion efficiencies are generated from mixtures of these electron donor assemblies which include the polymers and, for example, the electron acceptor, PCBM (a fullerene derivative [6,6]-phenyl-C61-butyric acid methyl ester).

Inks for Printing Photoactive Films and Photoactive Films Formed Thereby

The polymer building blocks and polymers described herein are advantageously soluble in a variety of solvents and can use used to make liquid compositions (inks) to form semiconductive ink compositions. Accordingly, provided herein are solutions comprised of building blocks of the polymers described herein and/or partially polymerized building blocks (oligomers) and/or fully polymerized polymers as described herein, and a suitable solvent. The inks are suitable for use in forming films (e.g. thin films) by techniques known in the art, e.g. by spray technology resembling that of ink-jet printers and/or modifications thereof such as those described in U.S. Pat. Nos. 8,597,973 and 8,071,875 and in United States patent application 20140000700, the entire contents of each of which are hereby incorporated by reference. The technology generally involves applying e.g. by spraying or otherwise coating the ink onto a substrate or support to form a film with desired dimensions, e.g. of a desired length, width and thickness.

Solvents which may be used to form the solutions described herein include, without limitation, dichloromethane, (DCM), tetrahydrofuran (THF), chloroform (CHCl₃), toluene, xylene, dimethylformamide (DNF), chlorobenzene, o-dichlorobenzene, and trichlorobenzene, dimethylsulfoxide (DMSO), methanol (MeOH) ethanol (EtOH) and water.

The solutions or inks that comprise the polymers, oligomers and or building blocks thereof may also comprise other useful components, e.g. various colorants, dopants, metals or metals ions, other polymers, surfactants, and additives. Films formed in this manner are photoactive and electrically conductive and suitable for use in variety devices, such as those described above (solar cells, transistors, etc.).

EXAMPLES

Example 1. Eumelanin-Inspired Core Derived from Vanillin: A New Building Block for Organic Semiconductors An eumelanin-inspired core derived from the natural product, vanillin (vanilla bean extract) was utilized for the synthesis of eumelanin inspired small molecules (4,7-disubstituted indoles) and polymers via Sonogashira cross coupling. The materials demonstrate that the methyl 4,7-dibromo-5,6-dimethoxy-N-methyl-1H-indole-2-carboxylate core can serve as a new building block for organic semiconductors.

Organic semiconductors have attracted considerable attention due to the promise of low cost, lightweight, and flexible large area electronic devices.[1] Most of these materials are derived from petroleum-based starting materials. Due to the increasing demand on oil, it would be advantageous to seek alternative sources for building blocks to develop new organic semiconductors.

In terms of chemical and functional diversity, nature is a great source of new building blocks for bioinspired organic semiconductors. One such inspiration is the biopolymer, melanin which is a class of naturally occurring pigments found in the hair, eyes, skin, and the brain of mammals and acts as a natural photoprotector against the harmful effects of UV radiation.[2] Eumelanin is the black-brown variety of melanin and exist as a heterogeneous network, formed by the oxidative polymerization of two monomers 5,6-dihydroxyindole (DHI) and 5,6-dihydroxyindole-2-carboxylic acid (DHICA) (FIG. 1).[3]

Extensive research has been done on the optical, electronic, physical, metal chelating, and structural properties of natural and synthetic eumelanins.[3,4] McGinness and Proctor's groundbreaking work on electrical switching established eumelanins as amorphous organic semiconductors.[5] These eumelanins have excellent light absorption ranging from 200 nm to 700 nm in the electromagnetic spectrum, electrical conductivity reaching $10^{-5}$ S cm$^{-1}$ and exhibit good charge mobility as high as $2.1 \times 10^{-3}$ cm$^2$ V$^{-1}$ s$^{-1}$.[6] Hence, it seems appropriate and fitting to utilize the eumelanin indole moiety as a platform for the development of new organic semiconductors.[2a]

Here, the synthesis of a eumelanin-inspired core molecule from the natural product, vanillin, is presented. The eumelanin inspired building block was designed so that functionalization on the 4,7-positions on the central indolic benzene ring can be feasible via transition metal-catalyzed cross-coupling reactions. Two new eumelanin-inspired compounds with interesting optoelectronic properties were synthesized by Sonogashira cross-coupling.

Figure 2:
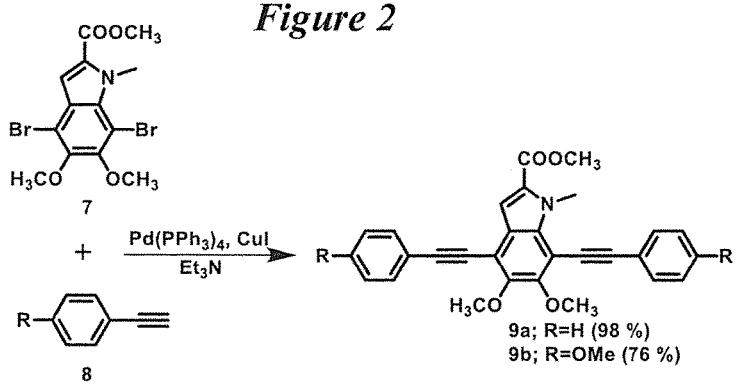
FIG. 2. Synthesis of compounds 9a and 9b (Scheme 2).
Figure 3:
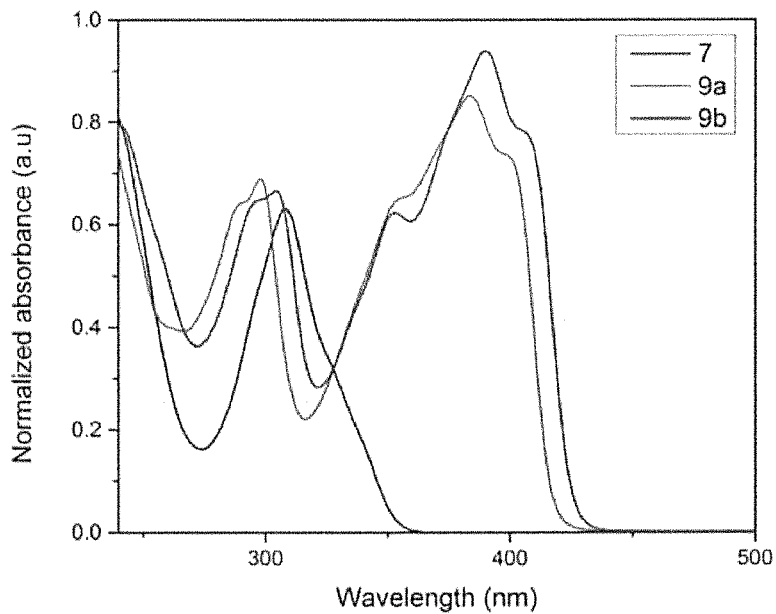
FIG. 3. The UV-vis absorption spectra of 7, 9a and 9b.

The synthesis of the methyl 4,7-dibromo-5,6-dimethoxy-Nmethyl-1H-indole-2-carboxylate (DBI) eumelanin-inspired core 7 is shown in Scheme 1 (depicted in FIG. 2). Vanillin (1) was methylated to give dimethoxybenzaldehyde (2), which was nitrated to yield 3.[7] Bromination of 3 using N-bromosuccinimide resulted in compound 4.[8] A modified procedure was used to synthesize the olefin 5 using methyl bromoacetate in aqueous sodium bicarbonate, followed by microwave-assisted Cadogan synthesis to afford 6.[9] Finally, the indole was N-methylated to avoid unwanted by-products during the cross coupling reactions. Compound 7 was synthesized with bromo groups at the 4 and 7 positions of the indole moiety so it could serve as a universal partner for metal-catalyzed coupling reactions. This approach allowed for the functionalization at the 4 and 7 positions with alkynyl substituents using Sonogashira crosscoupling (Scheme 2, depicted in FIG. 3). The ethynyl group was chosen because of its ability to alter optoelectronic properties by extended effective π-conjugation length.[10]

The coupling reaction was carried out using Pd(PPh$_3$)$_4$, CuI and triethylamine (Et$_3$N) as solvent and base to afford the products 9a and 9b in high yields.[11] X-ray quality crystals of 9a were grown from a vapour diffusion of ether and dichloromethane solutions (see ESI† for the crystallographic data).

Figure 4:
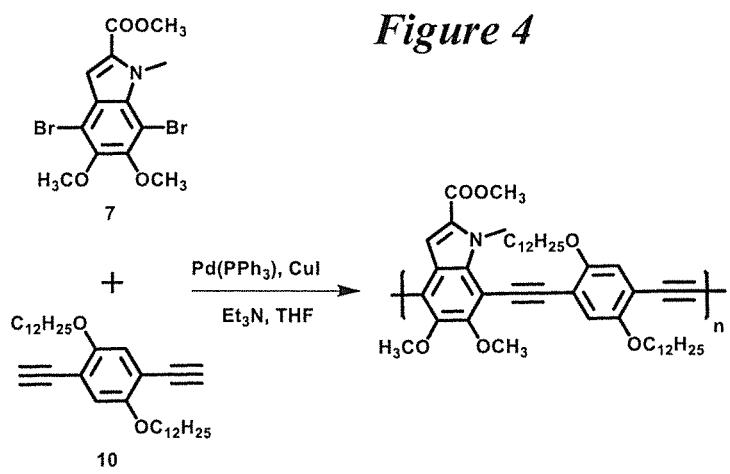
FIG. 4. Synthesis of the eumelanin-inspired polymer (Scheme 3).

The UV-VIS absorption (FIG. 4) and photoluminescence (PL) of the eumelanin-inspired small molecules were investigated and summarized in the Table 1. The 4,7-substituted eumelanin inspired small molecules 9a and 9b featured red-shifted absorbance maxima due to extended conjugation of the system compared to the unsubstituted core 7 (abs $\lambda_{max}$ 308 nm). While the absorption band at lower wavelength (~300 nm) corresponds to the indole core, the ethynyl substitution extends the conjugation through the eumelanin inspired core which resulted in the absorption band ca. 400 nm. Moreover, the incorporation of the methoxy group at the para position of the phenyl ring (9b) resulted in a slight red shift in absorption spectrum compared to 9a. The DBI core displayed very weak fluorescence whereas 9a and 9b had PL maxima of 436 nm and 449 nm, respectively. The PL quantum yields of the 9a and 9b in dilute chloroform solutions were 0.82 and 0.91, respectively. Optical bandgaps were estimated from the onset of the absorption are shown in Table 1. The compound 7 had a bandgap of 3.25 eV and as expected the 4,7-substituted molecules 9a and 9b with extended conjugation showed reduced optical bandgaps of 2.94 and 2.87 eV, respectively.

TABLE 1

Optical and electrochemical properties of 7, 9a and 9b

| | $\lambda_{abs}^b$ (nm) | $\lambda_{em}^b$ (nm) | $\Phi_{re}^c$ | $E_{opt}^d$ (eV) | $E_{ox}^e$ (eV) | $E_{ox}^e$ (eV) | $E_{ox-red}$ (eV) |
|---|---|---|---|---|---|---|---|
| 7 | 308$^a$ | — | — | −3.35 | −5.76 | −2.87 | 2.89 |
| 9a | 384$^a$, 209, 239 | 436 | 0.82 | −2.94 | −5.55 | −2.70 | 2.85 |
| 9b | 390$^a$, 353, 304, 241 | 449 | 0.91 | −2.87 | −5.45 | −2.65 | 2.80 |

$^a\lambda_{max}$.
$^b$Measured in dilute chloroform.
$^c$Quantum yields measured in dilute chloroform solutions relative to quinine sulfate.
$^d$Measured from onset of absorption.
$^e$Calculated from onset of oxidation and reduction potential.

Cyclic voltammetry measurements were carried out in dry degassed acetonitrile under inert atmosphere using 0.1 M tetrabutylammonium hexafluorophosphate as the supporting electrolyte. A Ag/Ag$^+$ reference electrode was calibrated against ferrocene/ferrocenium (Fc/Fc$^+$) redox couple. The HOMO and LUMO (highest occupied molecular orbital and lowest unoccupied molecular orbital) energy values were calculated from the onset of the first oxidation and reduction potentials from the equations $E_{HOMO}$ (eV)=−[$E_{ox}^{onset}$−$E_{1/2}$ (Fc/Fc$^+$)+4.8] and $E_{LUMO}$ (eV)=−[$E_{red}^{onset}$−$E_{1/2}$ (Fc/Fc$^+$)+4.8], where $E_{1/2}$ (Fc/Fc$^+$) was the cell correction. The oxidation potential for DBI was −5.76 eV whereas 9a and 9b values correspond to −5.55 eV and −5.45 eV, respectively. Both 9a and 9b had higher LUMO energy levels than the DBI core (see Table 1). The calculated bandgap values were 2.89 eV, 2.85 eV and 2.80 eV for the 7, 9a and 9b, respectively, which indicated that the electron donating methoxy group resulted in the lower bandgap. This trend was also observed for the estimated optical bandgaps. From the voltammograms (S18), it was evident that the compounds had irreversible reduction and oxidation potentials.

To further demonstrate the utility of the eumelanin inspired core 7 as a building block for organic semiconductors, a model conjugated polymer was synthesized of via Sonogashira crosscoupling conditions. The polymerization of 7 and 1,4-bis(dodecyloxy)-2,5-diethynylbenzene (10), was selected because of the similarity of 10 to methoxy monomer 9b. This resulted in a red polymer with 36% yield (Scheme 3, shown in FIG. 5). The polymer was soluble in various solvents including TI-F, chloroform, toluene and chlorobenzene, and the structure was confirmed by $1^H$ NMR spectroscopy. Gel permeation chromatography showed a number average molecular weight (Mn) of 13.6 kDa, PDI=1.88. The photophysical characteristics of the polymer, both in dilute solutions and thin films, were examined using UV-VIS absorption and fluorescence spectroscopy. The polymer exhibited an absorption maximum at 485 nm in solution and a red-shifted absorption maximum of 526 nm for polymer thin films. Green fluorescence was observed for the polymer with an emission maximum at 508 nm and the quantum yield in dilute chloroform was 0.60. The electrochemical properties of the polymer were investigated. The HOMO level for the polymer was similar to 9b (−5.47 eV); however, LUMO level was deepened to −3.44 eV. The morphology of the polymer thin film was characterized by AFM, as shown in the ESI.† The polymer thin film appears to be composed of packed small grains varying in size and shape averaging 20 nm in diameter. Currently, work is continuing to optimize the polymerization conditions in order to improve yield and obtain higher molecular weight polymers.

In summary, this example shows that an eumelanin-inspired core molecule derived from vanillin can serve as a building block for the development of eumelanin-inspired organic semiconductors. Two new eumelanin-inspired small molecules were synthesized in good yields. These materials exhibited red-shifted absorption and emission compared to the eumelanin-inspired core DBU This is attributed to the extended conjugation due to the phenyleneethynylene linkage. Moreover, an eumelanin-inspired polymer was synthesized which showed promise for optoelectronic devices. Current efforts focus on the synthesis and evaluation of optical and electronic properties of oligomers and polymers based on the eumelanin-inspired core moieties.

REFERENCES 1. (a) Y. Lin, Y. Li and X. Zhan, Chem. Soc. Rev., 2012, 41, 4245; (b) Q. Huang and H. Li, Chin. Sci. Bull., 2013, 58, 2677; (c) S. Allard, M. Forster, B. Souharce, H. Thiem and U. Scherf, Angew. Chem., Int. Ed., 2008, 47, 4070; (d) A. Facchetti, Chem. Mater., 2010, 23, 733; (e) A. C. Grimsdale, K. Leok Chan, R. E. Martin, P. G. Jokisz and A. B. Holmes, Chem. Rev., 2009, 109, 897; (f) S. W. Thomas, G. D. Joly and T. M. Swager, Chem. Rev., 2007, 107, 1339; (g) B. C. Thompson and J. M. J. Fre´chet, Angew. Chem., Int. Ed., 2008, 47, 58.
2. (a) A. Pezzella and J. Wu¨nsche, Organic Electronics, Wiley-VCH Verlag GmbH & Co. KGaA, 2013, pp. 91-137; (b) M. d'Ischia, K. Wakamatsu, A. Napolitano, S. Briganti, J.-C. Garcia-Borron, D. Kovacs, P. Meredith, A. Pezzella, M. Picardo, T. Sarna, J. D. Simon and S. Ito, Pigm. Cell Melanoma Res., 2013, 26, 616; (c) G. Prota, Melanins and Melanogenesis, Academic Press, New York, 1992.
3. P. Meredith and T. Sarna, Pigm. Cell Res., 2006, 19, 572.
4 (a) M. M. Jastrzebska, S. Jussila and H. Isotalo, J. Mater. Sci., 1998, 33, 4023; (b) A. B. Mostert, K. J. P. Davy, J. L. Ruggles, B. J. Powell, 1. R. Gentle and P. Meredith, Langmuir, 2009, 26, 412; (c) A. Corani, A. Huijser, T. Gustavsson, D. Markovitsi, P.-Å. Malmqvist, A. Pezzella, M. d'Ischia and V. Sundstro¨m, J. Am. Chem. Soc., 2014, 136, 11626; (d) J. Wuensche, F. Cicoira, C. F. O. Graeff and C. Santato, J. Mater. Chem. B, 2013, 1, 3836; (e) M. d'Ischia, A. Napolitano, A. Pezzella, P. Meredith and T. Sarna, Angew. Chem., Int. Ed., 2009, 48, 3914; (f) Y. J. Kim, W. Wu, S.-E. Chun, J. F. Whitacre and C. J. Bettinger, Adv. Mater., 2014, 26, 6572; (g) M. Abbas, F. D'Amico, L. Morresi, N. Pinto, M. Ficcadenti, R. Natali, L. Ottaviano, M. Passacantando, M. Cuccioloni, M. Angeletti and R. Gunnella, Eur. Phys. J. E: Soft Matter Biol. Phys., 2009, 28, 285.
5. (a) J. McGinness, P. Corry and P. Proctor, Science, 1974, 183, 853; (b) J. E. McGinness, Science, 1972, 177, 896.
6. (a) P. R. Crippa, V. Cristofoletti and N. Romeo, Biochim. Biophys. Acta, 1978, 538, 164; (b) J. P. Bothma, J. de Boor, U. Divakar, P. E. Schwenn and P. Meredith, Adv. Mater., 2008, 20, 3539.
7. C. A. Fetscher, Org. Synth., 1953, 33, 65.
8. P. B. Huleatt, J. Lau, S. Chua, Y. L. Tan, H. A. Duong and C. L. L. Chai, Tetrahedron Lett., 2011, 52, 1339.
9. E. C. Creencia, M. Kosaka, T. Muramatsu, M. Kobayashi, T. Iizuka and T. Horaguchi, J. Heterocycl. Chem., 2009, 46, 1309.
10. (a) U. H. F. Bunz, Chem. Rev., 2000, 100, 1605; (b) L. Capelli, P. Manini, A. Pezzella and M. d'Ischia, Org. Biomol. Chem., 2010, 8, 4243; (c) L. Capelli, P. Manini, A. Pezzella, A. Napolitano and M. d'Ischia, J. Org. Chem., 2009, 74, 7191; (d) C. Li and Y. Li, Macromol. Chem. Phys., 2008, 209, 1541; (e) A. Kawada, T. Nagahama, H. Hayashida and K. Masutani, PCT Int. Appl., WO2014156342 A1, 2014; (f) U. Berens, F. Bienewald and H. J. Kirner, PCT Int. Appl., WO 2007068618 A1, 2007; (g) R. Katakura, K. Hirai and H. Kita, Jpn. Kokai Tokkyo Koho, 2007, 35.
11 S. Atobe, M. Sonoda, Y. Suzuki, T. Yamamoto, H. Masuno, H. Shinohara and A. Ogawa, Res. Chem. Intermed., 2013, 39, 359.

Example 2. Synthesis of Additional Small Molecules Using the DBI Core

Figure 5:
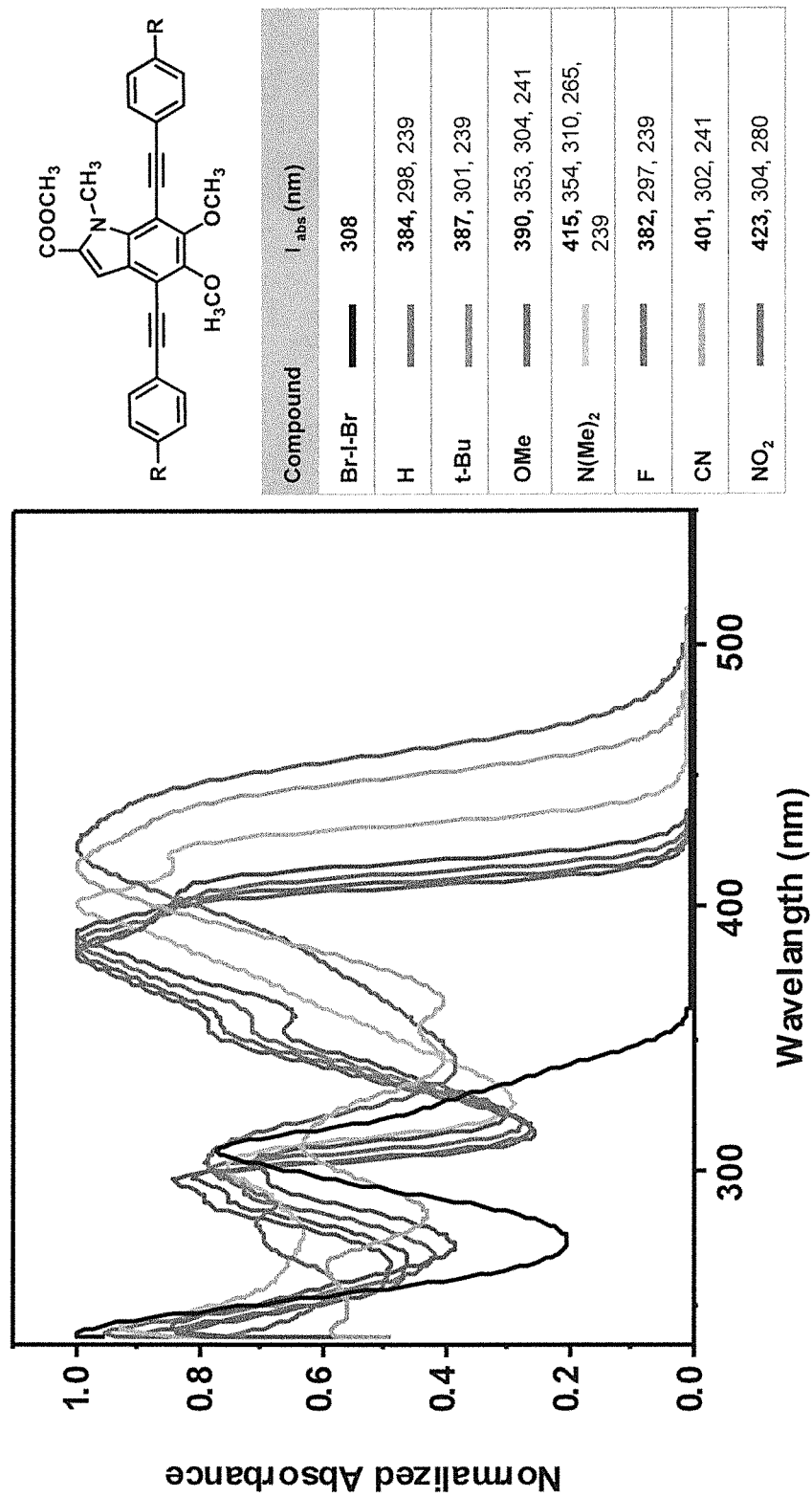
FIG. 5. Absorption spectra (in solution) of exemplary small molecules formed by functionalizing a DBI core.
Figure 6:
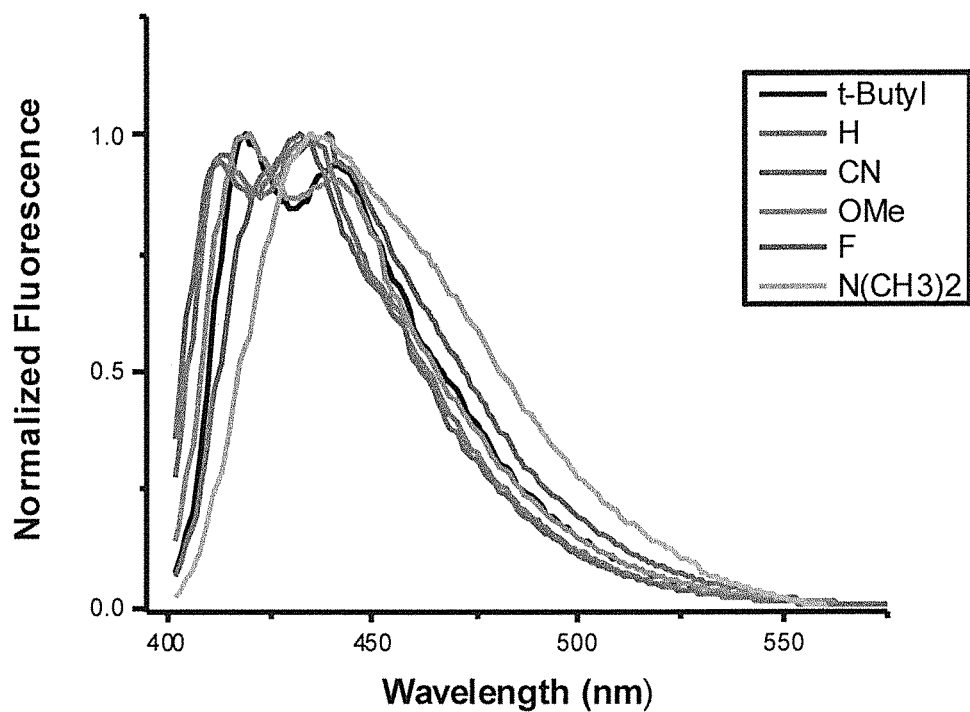
FIG. 6. Emission spectra (in solution) of exemplary small molecules formed by functionalizing a DBI core.
Figure 7:
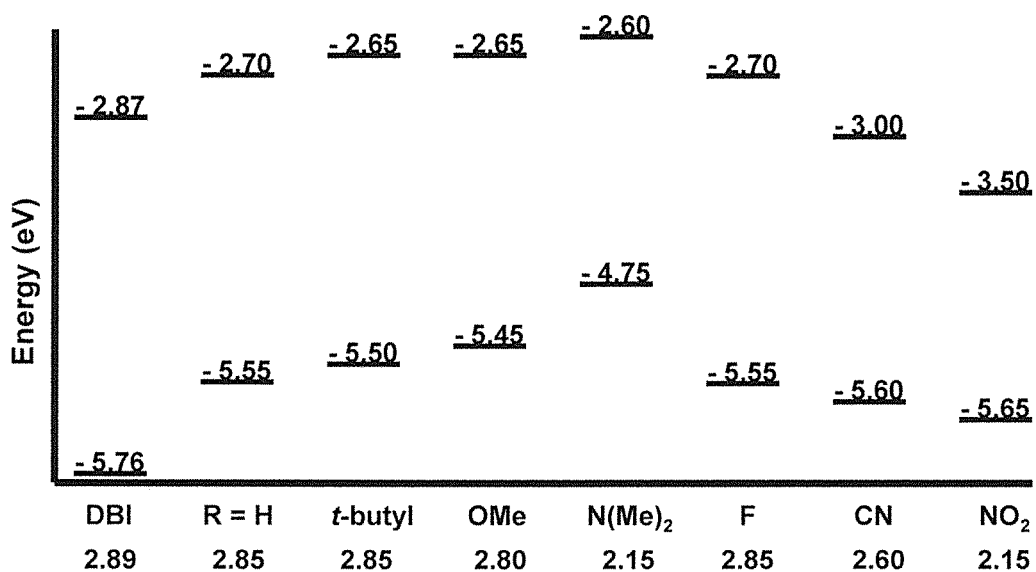
FIG. 7. HOMO and LUMO (highest occupied molecular orbital and lowest unoccupied molecular orbital) energy values of exemplary small molecules formed by functionalizing a DBI core.

Additional exemplary small molecules were formed by varying the R group at positions 4 and 7 of DBI. In various syntheses, R was Br (parent DBI molecule), H, t-butyl, O-methyl, N(methyl)$_2$, F, CN and NO$_2$. The absorption spectra of the resulting small molecules are depicted in FIG. 5, the emission spectra of selected compounds are presented in FIG. 6, and HOMO and LUMO values are presented in FIG. 7.

This example shows that the parent DBI core molecule can be successfully substituted at positions 4 and 7 with a wide variety of chemical groups with differing properties, and the resulting small molecules each display useful absorption and emission properties. The small molecules serve to demonstrate that the optical and electronic properties of DBI can be tuned by simple substituting at the 4 and 7 positions on the indole ring in addition to the electron donating or withdrawing ability of the R group at the para position the benzene ring. Moreover, some of these compounds exhibit a change in color at different pH values and upon metal binding and so can be employed in a variety of applications related to the measurement of pH and the detection of metals.

Example 3. Design and Synthesis of Well-Defined, Soluble Eumelanin-Inspired Polymers The DBI core molecule was successfully used to synthesize a variety polymer building blocks and polymers with useful photovoltaic properties.

Figure 8A:
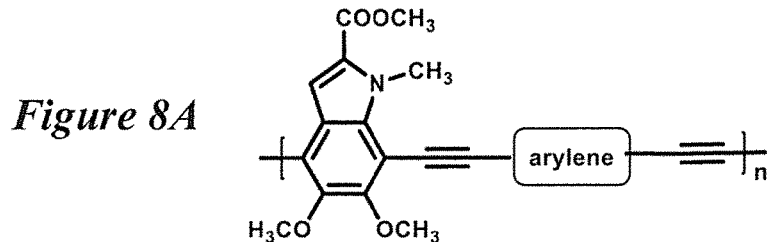
FIGS. 8A and B. A, generic arylene polymer; B, synthesis scheme for two exemplary arylene polymers.
Figure 8B:
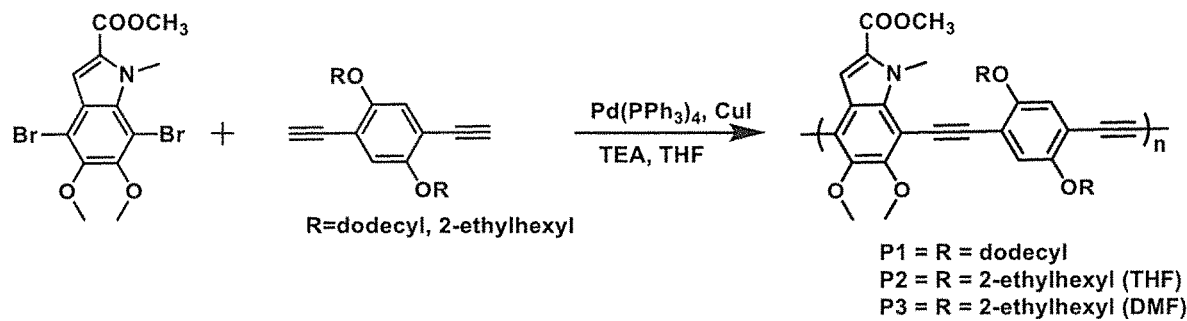

Arylene Polymers:

FIG. 8A depicts a generic arylene polymer subunit and Figure B depicts an representative synthesis scheme in which variable R groups (e.g. dodecyl and 2-ethylhexyl) are incorporated into the polymers. The resulting polymers were soluble in CHCl$_3$, tetrahydrofuran (THF), toluene and chlorobenzene Table 2 shows the solubility data obtained for THF.

TABLE 2

Solubility of arylene polymers in CHCl$_3$ and THF

|  | R = Dodecyl (THF) | R - Ethylhexyl (THF) | R - Ethylhexyl (DMF) |
|---|---|---|---|
| Mn* (kDa) | 13.6 | 8.9 | 5.8 |
| Mw** (kDa) | 25.5 | 17.6 | 10.0 |
| PDI*** | 1.88 | 1.97 | 1.92 |
| Yield (%) | 36 | 17 | 13 |

Figure 9A:
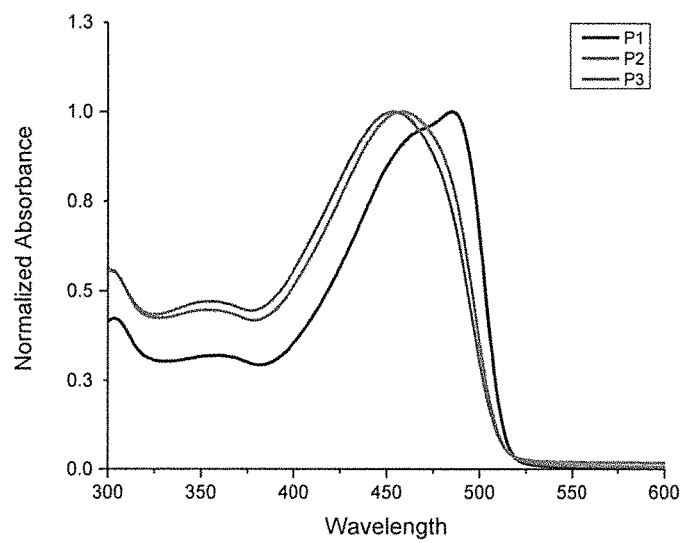
FIGS. 9A and B. Absorbance of the polymers in which R=dodecyl and 2-ethylhexyl A, in solution and B, as a thin film. P1=dodecyl in THF; P2=2-ethylhelxy in THF; P3=2-ethylhelxy in DMF.
Figure 9B:
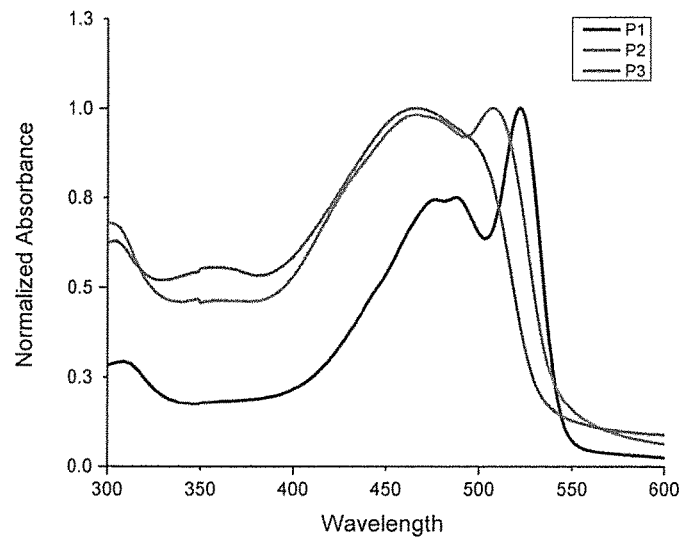

*Number average molecular weight measured by gel permeation chromatography:
**Number average molecular weight measured by gel permeation chromatography:
***Polydispersity index FIG. 9 shows absorbance of the polymers in solution (A) and as a thin film (B), and Table 3 provides related data.

TABLE 3

Absorbance parameters

|  | P1 R = dodecyl | P2 R = ethylhexyl (THF) | P3 R = ethylhexyl (THF) |
|---|---|---|---|
| $\lambda_{max}$ (solution) | 485 nm | 462 nm | 454 nm |
| $\lambda_{max}$ (film) | 485 nm | 507 nm | 465 nm |
| $\lambda_{ems}$ (solution) | 485 nm | 505 nm | 503 nm |
| Eg (eV) | 2.41 | 2.42 | 2.43 |

Poly(Indolylene Ethynylene) Polymers

Figure 10A:
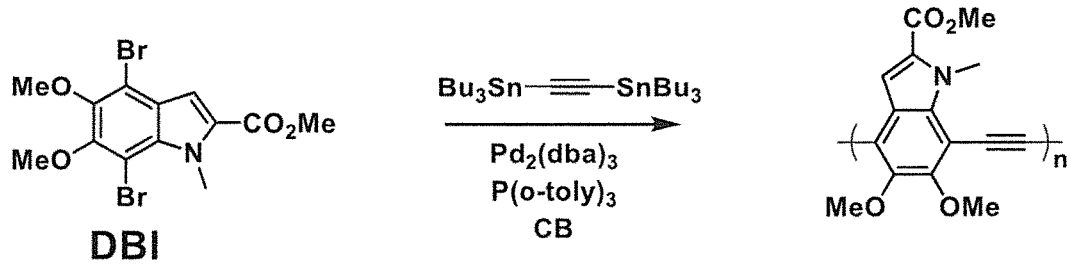
FIGS. 10A and B. A, synthesis scheme; B, absorbance spectrum for an exemplary poly(indolylene ethylnylene) polymer.
Figure 10B:
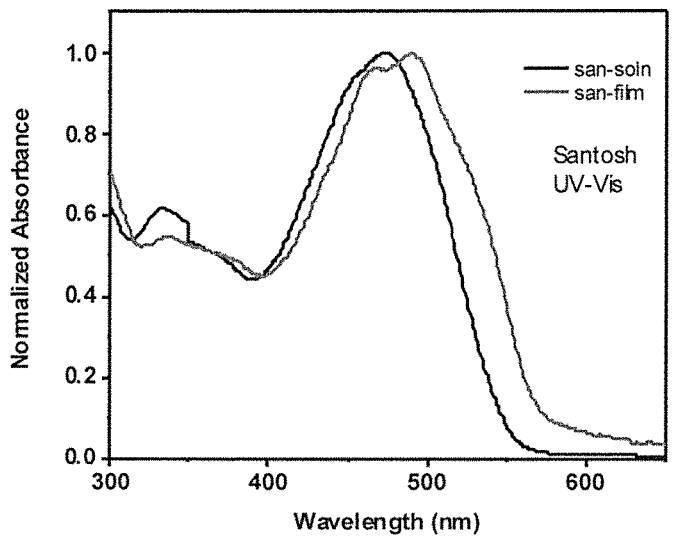

An exemplary poly(indolylene ethynylene) polymer was made using DBI as the core molecule. The resulting polymer was soluble in common solvents such as CHCl$_3$ and dichloromethane (DCM) and exhibited good film-forming properties. The synthesis scheme is shown in FIG. 10A and absorbance data is presented in FIG. 10B. Tables 4 and 5 present physical and absorbance characteristics of the polymer, respectively.

TABLE 4

Physical characteristics of a poly(indolylene ethylnylene) polymer

| Mn (kDa) | 4.0 |
| Mw (kDa) | 8.5 |
| PDI | 1.88 |
| Yield (%) | 36 |

TABLE 5

Absorbance characteristics of a poly(indolylene ethylnylene) polymer

| $\lambda_{max}$ (solution) | 475 nm |
| $\lambda_{max}$ (film) | 491 nm |
| $\lambda_{ems}$ (solution) | 525 nm |

Poly(Arylene Vinylene) Polymers

Figure 11A:
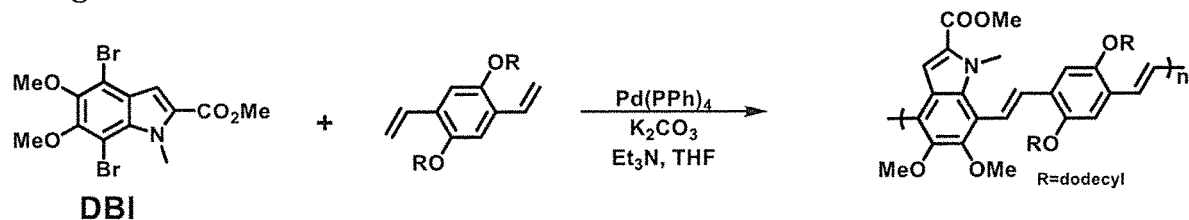
FIG. 11 A-C. A, representative synthesis scheme for a poly(arylene vinylene) polymer in which R=dodecyl; B, absorbance data; C, fluorescence data for the polymer.
Figure 11B:
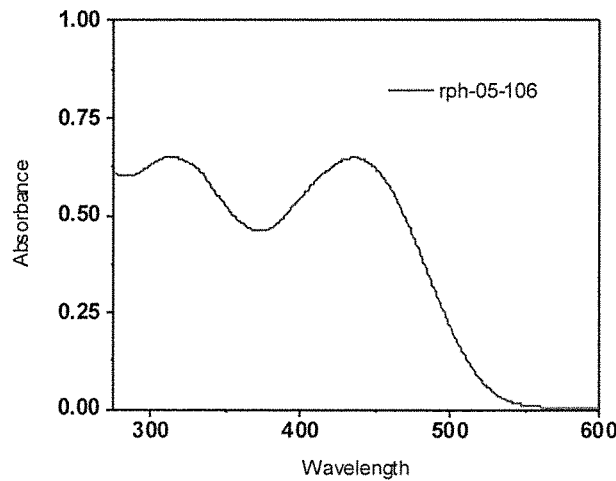
Figure 11C:
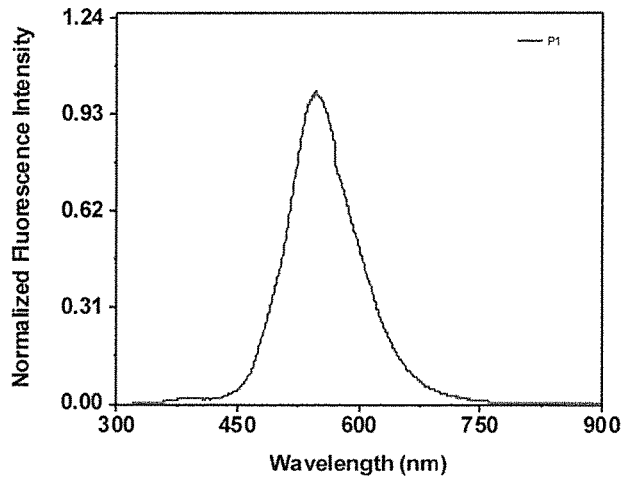

Poly(arylene vinylene) polymers were made using DBI as the core molecule. The resulting polymers were soluble in common solvents such as CHCl$_3$, THF, DCM and toluene, and exhibited good film-forming properties. A representative synthesis scheme for a polymer in which R=dodecyl is shown in FIG. 11A and absorbance and fluorescence data is presented in FIGS. 11B and C, respectively. Tables 6 and 7 present physical and absorbance characteristics, respectively, of a poly(arylene vinylene) polymer in which R=dodecyl

TABLE 6

Physical characteristics of a poly(arylene vinylene) polymer in which R = dodecyl in CHCl$_3$ solvent

| Mn (kDa) | 413 |
| Mw (kDa) | 26 |
| PDI | 2.0 |
| Yield (%) | 39 |

TABLE 7

Absorbance characteristics of a poly(indolylene ethylnylene) polymer

| $\lambda_{max}$ (solution) | 435 nm |
| $\lambda_{ems}$ (solution) | 547 nm |

Figure 12:
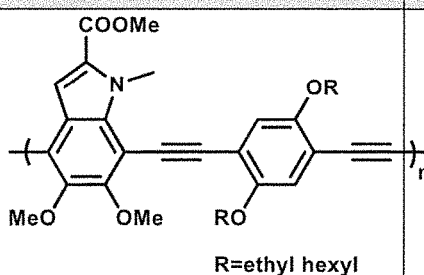
FIG. 12 depicts the solvatochromic properties of selected DBI-polymers. S: soluble, P: partly soluble and I: insoluble in a particular solvent.

FIG. 12 depicts the solvatochromic properties of selected DBI-polymers. As can be seen, the polymers have diverse chromic (optical) properties in different solvents mainly due the polarity of the solvent, an important factor when fabricating optical devices.

In summary, this Example shows that a wide variety of photoactive polymers with semiconductor properties can be made in good yield and in a relatively facile manner, starting from the core structure DBI, which in turn is synthesized beginning with the plant oil vanillin.

Example 4. Alternative DBI Synthesis Method

Figure 13:
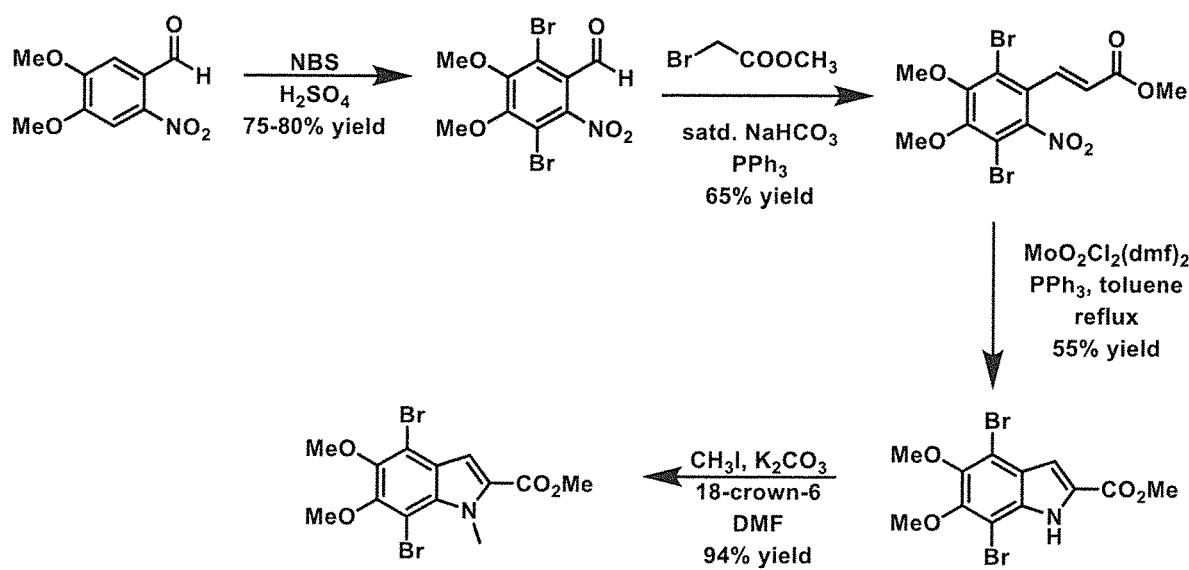
FIG. 13. Exemplary alternative synthetic scheme for DBI.

In some aspects, DBI is synthesized from the natural product, vanillin (e.g. as extracted from vanilla beans). However, those of skill in the art will recognize that other alternative synthetic schemes may be employed to arrive at this same novel molecule. An exemplary alternative synthetic scheme is presented in FIG. 13. As can be seen, in this alternative scheme, the starting material that was used is 6-nitroveratraldhyde which is an intermediate in the vanilla synthesis route. This Example shows that DBI can be synthesized by alternative routes that do not use vanillin as a starting material.

Example 5. "Black" Photoactive Materials for Organic Solar Cells: Eumelanin-Based Polymers Eumelanin-based synthetic polymers described herein are new light absorbing donors which absorb sunlight over a broad region (400-800 run) similar to the natural biopolymer, and broader than that of rr-P3HT. Given the synthetic eumelanin core structure, the opportunity to decorate the polymer at multiple sites is available via the R positions of the DBI starting material, which can be exploited to yield robust, processable polymers with tunable light absorption, durability and longevity.

Accordingly, new, highly light-absorbing active layers for enhanced solar power conversion efficiencies are generated from a mixture of electron donor assemblies comprising the polymers described herein and the electron acceptor, PCBM (the fullerene derivative [6,6]-phenyl-C61-butyric acid methyl ester). A schematic illustration of an organic solar cell utilizing these components is shown in FIG. 14. Accordingly, also provided herein are compositions comprising one or more (e.g. at least one) polymer as described herein (or repeat unit or oligomer thereof) and graphene or graphene oxide, generally in the form of, for example, a fullerene or a carbon nanotube. Exemplary fullerenes include but are not limited to: [6,6]-phenyl-C61-butyric acid methylester ($PC_{61}BM$), [6,6]-phenyl-C71-butyric acid methylester ($PC_{71}BM$), indene-$C_{60}$ ($IC_{60}BA$), and indene-$C_{70}$ ($IC_{70}BA$).

Additional details of the invention may be found in one or more appendices attached hereto, the disclosure(s) of which are incorporated herein by reference as if fully set out at this point.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e. g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be 10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e. g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

While this invention is susceptible of embodiment in many different forms, there is shown in the drawings, and is herein described in detail, some specific embodiments. It should be understood, however, that the present disclosure is to be considered an exemplification of the principles of the invention and is not intended to limit it to the specific embodiments or algorithms so described. Those of ordinary skill in the art will be able to make various changes and further modifications, apart from those shown or suggested herein, without departing from the spirit of the inventive concept, the scope of which is to be determined by the following claims.

Further, it should be noted that terms of approximation (e. g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. A polymer of Formula III

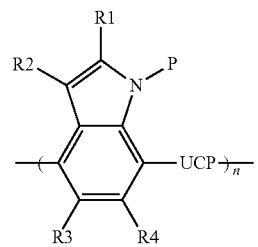

Formula III where R1, R2, R3 and R4 vary independently and may be the same or different, and can be H; substituted or unsubstituted alkylester; substituted or unsubstituted alkoxy:
P is H or $CH_3$;
UCP is present and is an unsaturated carbon pair which is connected indirectly to a repeat unit of the polymer through a substituted aromatic; and
n ranges from about 10 to about 1000.

2. The polymer of claim 1, wherein:
R1 is $COOCH_3$;
R2 is H;
R3 and R4 are $OCH_3$;
P is $CH_3$;
UCP is a triple bond;
the substituted aromatic is arylene; and
the polymer has the structure

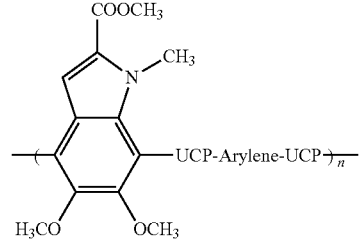

3. The polymer of claim 2, wherein the arylene is a substituted polycyclic aromatic hydrocarbon.

* * * * *